US007531202B2

(12) United States Patent
Moein

(10) Patent No.: US 7,531,202 B2
(45) Date of Patent: May 12, 2009

(54) NOZZLE AND METHOD FOR USE IN COATING A STENT

(75) Inventor: Mohammed E. Moein, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 32 days.

(21) Appl. No.: 11/454,571

(22) Filed: Jun. 16, 2006

(65) Prior Publication Data

US 2006/0240178 A1 Oct. 26, 2006

Related U.S. Application Data

(62) Division of application No. 10/366,784, filed on Feb. 13, 2003, now Pat. No. 7,087,115.

(51) Int. Cl.
*A61L 33/00* (2006.01)
*B05D 1/02* (2006.01)
*B05D 7/14* (2006.01)
*B05C 5/02* (2006.01)
*B05B 7/06* (2006.01)

(52) U.S. Cl. ...................... 427/2.1; 427/2.24; 427/2.25; 427/2.26; 427/425; 427/427.4; 427/427.5; 118/300; 118/319; 118/320; 118/313; 239/290; 239/296

(58) Field of Classification Search ................ 427/2.24, 427/425, 2.1, 2.25; 118/300, 313, 319–320; 239/290, 291, 296
See application file for complete search history.

(56) References Cited

U.S. PATENT DOCUMENTS 2,647,017 A 7/1953 Coulliette
3,735,778 A * 5/1973 Garnier ...................... 137/896
4,132,357 A 1/1979 Blackinton
4,146,900 A 3/1979 Arnold
4,733,665 A 3/1988 Palmaz
4,800,882 A 1/1989 Gianturco
4,886,062 A 12/1989 Wiktor
4,932,353 A 6/1990 Kawata et al.
4,967,606 A 11/1990 Wells et al.
5,015,505 A 5/1991 Cetnar
5,127,362 A 7/1992 Iwatsu et al.
5,225,750 A 7/1993 Higuchi et al.
5,368,560 A 11/1994 Rambo et al.
5,464,650 A 11/1995 Berg et al.

(Continued)

FOREIGN PATENT DOCUMENTS

EP 0 970 711 1/2000

(Continued)

OTHER PUBLICATIONS

U.S. Appl. No. 10/322,255, filed Dec. 17, 2002, Chen et al.

(Continued)

*Primary Examiner*—William Phillip Fletcher, III
*Assistant Examiner*—Cachet I Sellman
(74) *Attorney, Agent, or Firm*—Squire, Sanders & Dempsey, L.L.P.

(57) ABSTRACT

A nozzle for use in a coating apparatus for the application of a coating substance to a stent is provided.

15 Claims, 3 Drawing Sheets

U.S. PATENT DOCUMENTS

| | | | | |
|---|---|---|---|---|
| 5,511,726 | A | 4/1996 | Greenspan et al. | |
| 5,527,337 | A | 6/1996 | Stack et al. | |
| 5,687,913 | A | 11/1997 | Robisch et al. | |
| 5,700,286 | A | 12/1997 | Tartaglia et al. | |
| 5,713,949 | A | 2/1998 | Jayaraman | |
| 5,741,554 | A | 4/1998 | Tisone | |
| 5,766,710 | A | 6/1998 | Turnlund et al. | |
| 5,769,883 | A | 6/1998 | Buscemi et al. | |
| 5,824,056 | A | 10/1998 | Rosenberg | |
| 5,837,313 | A | 11/1998 | Ding et al. | |
| 5,843,172 | A | 12/1998 | Yan | |
| 5,869,127 | A | 2/1999 | Zhong | |
| 5,873,904 | A | 2/1999 | Ragheb et al. | |
| 5,980,972 | A | 11/1999 | Ding | |
| 5,984,449 | A | 11/1999 | Tajika et al. | |
| 6,056,993 | A | 5/2000 | Leidner et al. | |
| 6,068,202 | A * | 5/2000 | Hynes et al. | 239/290 |
| 6,096,070 | A | 8/2000 | Ragheb et al. | |
| 6,121,027 | A | 9/2000 | Clapper et al. | |
| 6,132,809 | A | 10/2000 | Hynes et al. | |
| 6,209,621 | B1 | 4/2001 | Treacy | |
| 6,214,407 | B1 | 4/2001 | Laube et al. | |
| 6,224,675 | B1 | 5/2001 | Prentice et al. | |
| 6,273,706 | B1 | 8/2001 | Günther | |
| 4,733,665 | C2 | 1/2002 | Palmaz | |
| 6,345,553 | B1 | 2/2002 | Adler et al. | |
| 6,395,326 | B1 | 5/2002 | Castro et al. | |
| 6,462,284 | B1 | 10/2002 | Hashimoto | |
| 6,491,666 | B1 | 12/2002 | Santini, Jr. et al. | |
| 6,743,462 | B1 * | 6/2004 | Pacetti | 427/2.24 |
| 6,811,805 | B2 * | 11/2004 | Gilliard et al. | 427/2.1 |

FOREIGN PATENT DOCUMENTS

| | | |
|---|---|---|
| WO | WO 98/23228 | 6/1998 |
| WO | WO 01/45763 | 6/2001 |
| WO | WO 01/52772 | 7/2001 |

OTHER PUBLICATIONS

"Impulse Jetting: About Us," http://www.impulsejetting.com/about.html, printed Dec. 18, 2000 (1 page).

"Impulse Jetting: Our Technology," http://www.impulsejetting.com/tech1.html, printed Dec. 18, 2000 (1 page).

"Consistent, precise spray valve system", EFO Inc., product information, (2004) 2 pgs.

Trident, Inc., http://www.tridetintl.com/subbody.html, printed Dec. 18, 2000 (4 pages).

World Precision Instruments, Inc., "Nanoliter 2000," http://www.wpi-europe.com/pumps/Nanoliter_Injector.html, printed Sep. 30, 2002 (4 pages).

World Precision Instruments, Inc., "Nonolite Injector," http://www.wpiinc.com/WPI_Web/Pumps/Nanoliter_Injector.html, printed Sep. 30, 2002 (3 pages).

World Precision Instruments, Inc., "Pneumatic PicoPumps," httm://www.wpi-europe.com/pumps/Pneumatic_PicoPumps.html, printed Sep. 30, 2002 (7 pages).

World Precision Instruments, Inc., "Pneumatic PicoPumps," http://www.wpiinc.com/WPI_Web/Pumps/Pneumatic_PicoPumps.html, printed Sep. 30, 2002 (6 pages).

World Precision Instruments, Inc., http://www.wpiinc.com/WPI_Web/Pumps/pneumatic_Fig.gif, printed Sep. 30, 2002 (1 page).

* cited by examiner

NOZZLE AND METHOD FOR USE IN COATING A STENT

CROSS-REFERENCE

This is a divisional application of application Ser. No. 10/366,784 filed on Feb. 13, 2003 now U.S. Pat. No. 7,087, 115.

TECHNICAL FIELD

This invention relates to an apparatus used in the process of coating a stent, and more particularly provides a nozzle for use in drug eluting stent spray coating.

BACKGROUND

Blood vessel occlusions are commonly treated by mechanically enhancing blood flow in the affected vessels, such as by employing a stent. Stents act as scaffolding, functioning to physically hold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by spraying the composition onto the stent. The solvent is allowed to evaporate, leaving on the stent surfaces a coating of the polymer and the therapeutic substance impregnated in the polymer.

A shortcoming of the above-described method of medicating a stent is the potential for coating defects and the lack of uniformity of the amount of composition material sprayed onto stents. While some coating defects can be minimized by adjusting the coating parameters, other defects occur due the shot to shot variation leading to excess composition being sprayed onto the stent. One cause of this shot to shot variation is the type of spray coater used. For example, a conventional EFD N1537 (EFD Inc. East Providence R.I.) spray coater uses a valve mechanism to dispense fluid and is most suitable for dispensing large amounts of composition (i.e., grams) and not small amounts (e.g., milligrams per spray cycle) as used in stent coating applications. Accordingly, conventional spray coaters tend to spray excess coating onto stents, which may stick to the stent, thereby leaving excess coating as clumps or pools on the struts or webbing between the struts.

Accordingly, a new nozzle for spraying coating is needed to minimize coating defects.

SUMMARY

The invention provides a nozzle assembly and method for use in coating a stent. In one embodiment, the nozzle assembly comprises an air chamber capable of receiving air from an atomizer for atomizing the composition as the composition is dispensed; a nozzle, coupled to the air chamber, having a plurality of air outlets capable of expelling air received from the atomizer via the air chamber to atomize the composition; and a hypotube disposed in the nozzle, the hypotube capable of dispensing the composition onto a stent.

The method comprises positioning a nozzle assembly having a hypotube disposed therein next to a stent, wherein the hypotube is in fluid communication with a reservoir containing a coating composition; discharging the coating composition from the reservoir out from the hypotube; and atomizing the coating composition into droplets as the coating composition is discharged out from the hypotube by expelling air from a plurality of air outlets in the nozzle assembly.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION

Figure 1:
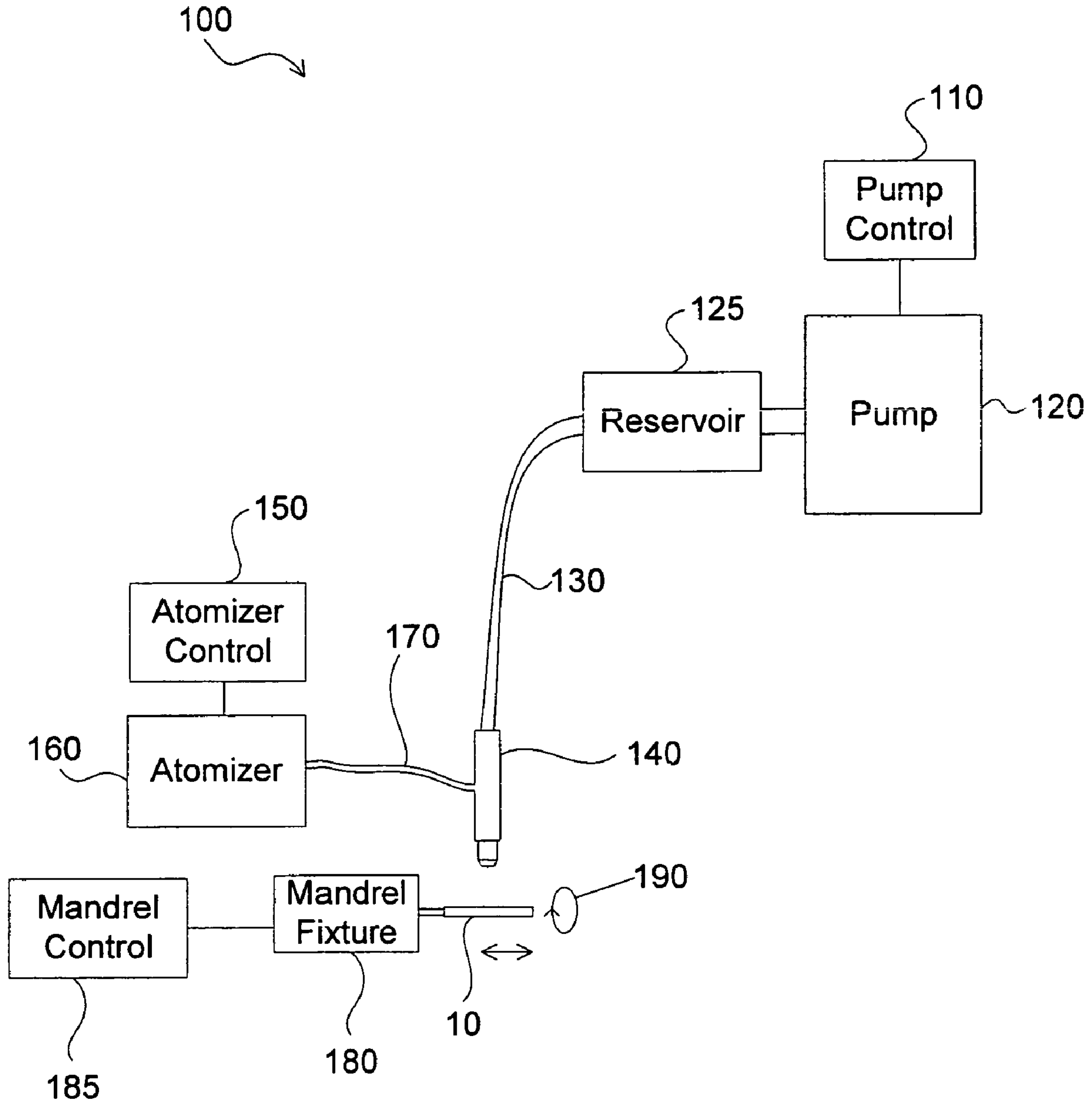
FIG. 1 is a block diagram illustrating a coating system for coating a stent with a composition.

FIG. 1 is a block diagram illustrating a coating system 100 for coating a stent 10 with a composition. The coating system 100 comprises a pump 120; a pump control 110; a reservoir 125; a nozzle assembly 140; an atomizer 160; an atomizer control 150; a mandrel fixture 180; and a mandrel fixture control 185. The pump control 110 is communicatively coupled to the pump 120 and controls the amount of fluid (also referred to interchangeably as coating substance or composition) dispensed by the pump 120 from the reservoir 125. The pump control 110 may include mechanical and/or electrical control mechanisms. In an embodiment of the invention, the pump control 110 is integrated with the pump 120.

The pump 120 pumps fluid from the reservoir 125, for coating the stent 10, to the nozzle assembly 140 via a tubing 130. The pump 120 may pump the fluid from the reservoir 125 at a rate of 0.15 cc/min, for example. In one embodiment of the invention, the pump 120 includes a syringe pump. In another embodiment of the invention, the pump 120 includes a gear pump. It will be appreciated that the pump 120 can comprise other types of pumps and/or combinations of pumps such as a positive displacement pump or a green pump.

The coating substance can include a solvent and a polymer dissolved in the solvent and optionally a therapeutic substance or a drug added thereto. Representative examples of polymers that can be used to coat a stent include ethylene vinyl alcohol copolymer (commonly known by the generic name EVOH or by the trade name EVAL); poly(hydroxyvalerate); poly(L-lactic acid); polycaprolactone; poly(lactide-co-glycolide); poly(glycerol-sebacate); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and mixtures and combinations thereof.

The therapeutic substance or drug can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), coichicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, dexamethasone, and rapamycin.

Figure 2:
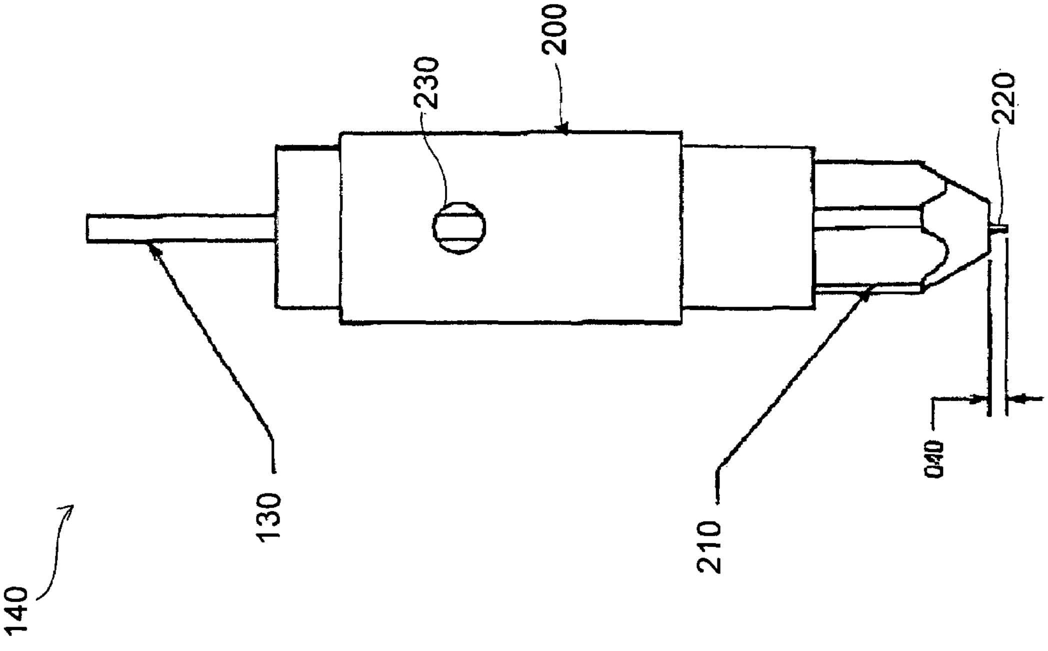
FIG. 2 is a side view illustrating the nozzle assembly of the coating system of FIG. 1 in accordance with an embodiment of the invention.

The atomizer 160 supplies high-pressure air to the nozzle assembly 140 via a tubing 170 coupled to an air inlet 230 (FIG. 2). This high-pressure air is used to atomize the composition dispensed from the nozzle assembly 140 onto the stent 10, as will be discussed in further detail below. The atomizer control 150 is communicatively coupled to the atomizer 160 and controls the pressure of the air dispensed from the atomizer 160 to the nozzle assembly 140. The atomizer control 150 can include electrical mechanisms, mechanical mechanisms, or a combination thereof to control the atomizer 160. In an embodiment of the invention, the atomizer control 150 and the atomizer 160 can be integrated into a single device.

The mandrel fixture 180 supports the stent 10 during a coating application process. In addition, the mandrel fixture 180 can include an engine so as to provide rotational motion about the longitudinal axis of the stent 10, as depicted by the arrow 190, during the coating process. Another motor can also be provided for moving the stent 10 in a linear direction, back and forth. The mandrel control 185 is communicatively coupled to the mandrel fixture 180 and controls movement of the stent 10. The type of stent that can be crimped on the mandrel fixture 180 is not of critical significance. The term stent is broadly intended to include self- and balloon-type expandable stents as well as stent-grafts.

The nozzle assembly 140, as will be discussed in further detail in conjunction with FIG. 2, receives the coating composition from the reservoir 125 via the tubing 130. In addition, the nozzle assembly 140 receives high-pressure air from the atomizer 160. During a stent coating application process, the nozzle assembly 140 dispenses composition onto stent 10. During the dispensing, high-pressure air from the atomizer 160 atomizes the composition, leading to a more uniform distribution on the stent 10.

It will be appreciated that the multiple control devices, i.e., the pump control 110, atomizer control 150, and mandrel control 185 can be combined into a single control device to simplify setting parameters for an operator.

FIG. 2 is a side view illustrating the nozzle assembly 140 of the coating system 100 of FIG. 1 in accordance with an embodiment of the invention. The nozzle assembly 140 comprises an air chamber 200; a nozzle 210; and a hypotube 220. In an embodiment of the invention, the air chamber 200 and nozzle 210 are formed out of a hypodermic syringe. The air chamber 200 can be made of polyethylene, glass, stainless steel and/or other materials. The air chamber 200 is cylindrical in shape and has a circular air inlet 230 to enable coupling of the tubing 170, which is in gaseous communication with the atomizer 160, so as to receive air for atomization. In an embodiment of the invention, the air chamber 200 includes a plurality of air inlets that are in gaseous communication with the atomizer 160.

In addition, the tubing 130 traverses an interior of the air chamber 200 and is in liquid communication with the reservoir 125 and the hypotube 220. The air chamber 200 will be discussed in further detail in conjunction with FIGS. 4 and 5.

The nozzle 210, which is coupled to the air chamber 200, is generally cylindrical in shape and has the hypotube 220 extending outwards about 0.040 inches from the bottom of the nozzle 210. The hypotube 220 is tubular in shape and can have a length of about 1 inch with an inner diameter of about 0.007 inches to about 0.008 inches and an outer diameter of about 0.016 inches. The nozzle 210 will be discussed in further detail in conjunction with FIGS. 6 and 7.

During a stent coating or other implantable medical device coating, the nozzle assembly 140 receives composition from the reservoir 125 via the tubing 130. The composition travels through the tubing 130 and enters the hypotube 220. The composition is then dispensed from the hypotube onto the stent 10. Further, as the composition is dispensed, the atomizer 160 supplies air to the nozzle assembly 140 via the tubing 170 to atomize the composition. The air flows through the air inlet 230 into the air chamber 200, which is gaseous communication with the nozzle 210. The air then enters the nozzle 210 and exits the nozzle 210 via the air outlets 300 (FIG. 3).

Figure 3:
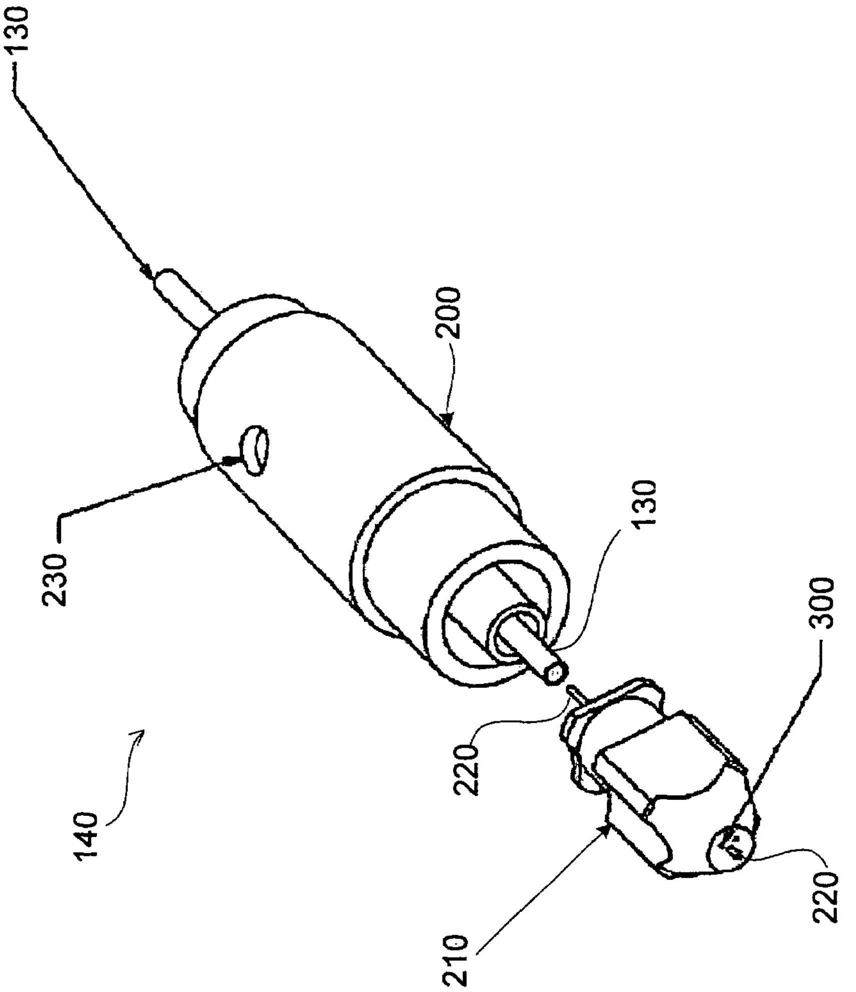
FIG. 3 is a disassembled perspective view illustrating the nozzle assembly.

FIG. 3 is a disassembled perspective view illustrating the nozzle assembly 140. The nozzle 210 includes four circular air outlets 300 for dispensing air for atomization of dispensed composition. The air outlets 300 circumscribe the hypotube 220 and enable external mixing of the composition dispensed from the hypotube 220 with air from the atomizer 160. The external mixing causes atomization of the dispensed composition, thereby causing more uniform coating of the stent 10. In an embodiment of the invention, the air outlets 300 can each have a diameter of approximately ⅛ of an inch. In another embodiment of the invention, additional or fewer air outlets 300 can be used. The air outlets 300 can be positioned equidistant from one another around the hypotube 220.

Generally, smaller atomized droplets of the composition, e.g., a fine mist, is preferable to large droplets of the composition so as to ensure an even coating on the stent 10. Droplet size is directly proportional to the diameter of the hypotube 220 orifice. Accordingly, a smaller needle orifice is superior for atomization than a larger diameter nozzle as used conventionally. More specifically, the standard median droplet diameter $$SMD \propto diameter_o U_R \frac{Mass_{fluid}}{Mass_{air}},$$

-continued wherein $$U_R = \frac{Velocity_{fluid}}{Velocity_{air}},$$

and wherein diameter$_o$ is the diameter of the hypotube 220 orifice. Accordingly, in addition to a small hypotube diameter, high air velocity and less fluid (e.g., composition) increases atomization of the fluid and therefore increases the even coating of the stent 10 with the fluid. Conventional nozzle assemblies that are designed to dispense grams of fluid per shot generally dispense large and uneven amounts of fluid per shot and so do not always enable adequate atomization. In contrast, the hypotube 220 can dispense small uniform amounts of fluids via a small diameter orifice, thereby enabling adequate atomization of the fluid to ensure even coating of the stent 10.

Further, the atomizing air from the air outlets 300 exits at a relatively high velocity compared to other designs, thereby causing greater atomization than the other designs. The relatively high velocity is necessitated by the small diameters of the air outlets 300, which force the air out at a high velocity as compared to a single large outlet or outlets.

Figure 4:
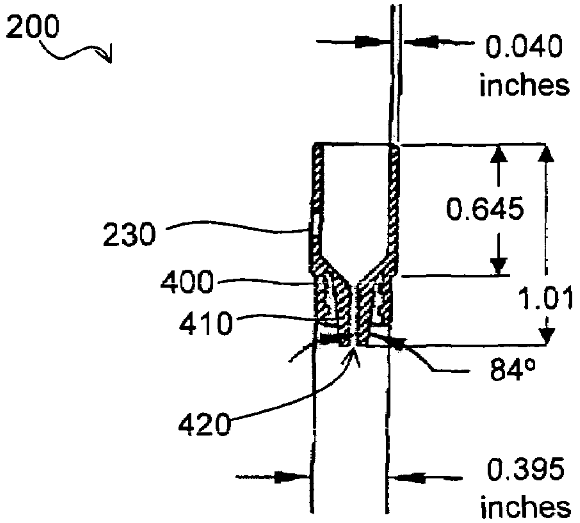
FIG. 4 is a cross section of the air chamber of the nozzle assembly.

FIG. 4 is a cross section of the air chamber 200 of the nozzle assembly 140. The air chamber can have a length of about 1 inch and a diameter of about 0.395 inches. The wall of the air chamber 200 can have a thickness of about 0.040 inches. In an embodiment of the invention, the air chamber 200 has a wall 400 having a grooved interior surface adapted for coupling the nozzle 210, which has a grooved exterior surface in one embodiment. In addition, the air chamber 200 includes a spout 410 for receiving the hypotube 220 via a spout opening 420 so that the hypotube 220 can come into liquid communication with the tubing 130. The spout 410 is located in the interior of the air chamber 200 and its exterior wall has an angle of inclination of about 84 degrees. In an embodiment of the invention, the tubing 130 can extend at least partially through the spout 410 and connect in a snug-fit manner over one end of the hypotube 220. The inner diameter of the spout 410 is greater than the outer diameter of the hypotube 220 thereby enabling atomizing air from the air chamber 200 to pass through the spout 410 to the nozzle 210.

Figure 5:
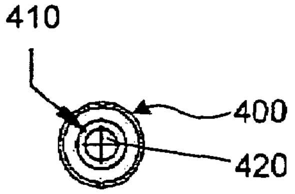
FIG. 5 is a bottom view of the air chamber.

FIG. 5 is a bottom view of the air chamber 200. The hypotube 220 can extend into the air chamber 200 via the spout opening 420, which is circular, so as to come into liquid communication with the tubing 130. Further, the interior surface of the wall 400 can include grooves or other mechanism (s) to removeably or permanently couple the nozzle 210 to the air chamber 200.

Figure 6:
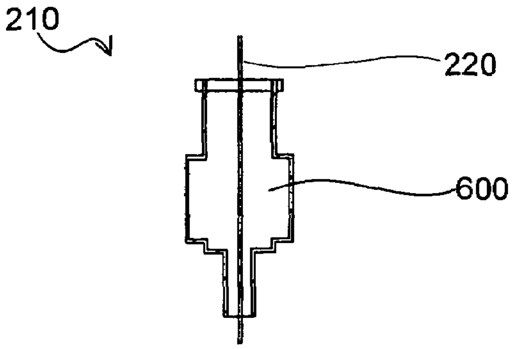
FIG. 6 is a cross section of the nozzle assembly.

FIG. 6 is a cross section of the nozzle 210 of the nozzle assembly 140. The hypotube 220 traverses the interior of the nozzle 210 and extends outwards from both the bottom and top of the nozzle 210. In addition, the nozzle 210 is shaped so as to have an interior region 600 for receiving atomizing air from the spout opening 420. The atomizing air can exit from the air outlets 300. The hypotube 220 can be permanently affixed within the nozzle 210 so that hypotube 220 can be maintained at the center of the air outlets 300. In one commercially applicable embodiment, the hypotube 220 is securely coupled, for example via an adhesive, to the spray end of the nozzle 210, out from which the hypotube 220 extends. This configuration enables the hypotube 220 to be permanently positioned at an equal distance from all of the air outlets 300. Accordingly, no adjustments are required when the nozzle 210 is coupled to the air chamber 200 for centering the hypotube 200 so that the application of air via the air outlets 300 is uniformly applied to the exiting composition.

Figure 7:
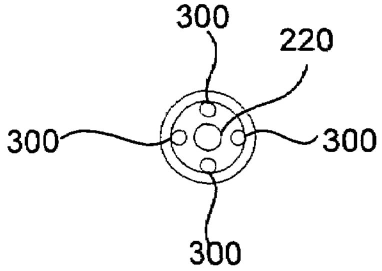
FIG. 7 is a bottom view of the nozzle.

FIG. 7 is a bottom view of the nozzle 210 illustrating the hypotube 220 positioned at the center of air outlets 300. The nozzle 210 having the hypotube 220 connected thereto is disposable and inexpensive to manufacture. Further advantages include that the nozzle 210 can be easily coupled to the chamber 200 and the tube 130 without the need of having to make adjustments to center the hypotube 220 with respect to the atomizing air outlet holes 300.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of coating a stent, comprising:

positioning a nozzle assembly having a hypotube next to a stent, wherein the hypotube is in fluid communication with a reservoir containing a coating composition;

discharging the coating composition from the reservoir out from the hypotube; and atomizing the coating composition into droplets as the coating composition is discharged out from the hypotube by expelling air from a plurality of air outlets in the nozzle assembly;

wherein the nozzle assembly includes an air chamber, and wherein the air expelled from the plurality of air outlets comes from the air chamber, and wherein the hypotube is disposed partially inside a tube that carries the coating composition and extends through the air chamber.

2. The method of claim 1, additionally comprising rotating the stent about the longitudinal axis of the stent.

3. The method of claim 1, wherein the composition is atomized external to the nozzle assembly.

4. The method of claim 1, wherein a portion of the hypotube extends out from the nozzle assembly.

5. The method of claim 1, wherein the composition includes a polymer dissolved in a solvent and optionally a therapeutic substance added thereto.

6. The method of claim 1, wherein the plurality of air outlets include air outlets that circumscribe the hypotube.

7. The method of claim 1, wherein the air outlets include four circular air outlets.

8. A method of coating a stent, comprising discharging a coating substance onto a stent from a nozzle assembly, the nozzle assembly comprising:

a chamber for receiving air for atomizing a stent coating substance;

an end cap replaceably connectable to one end of the chamber, the end cap having at least two holes for expelling the air received in the chamber; and a needle permanently affixed to the end cap for discharging the coating substance, wherein a segment of the needle extends out from the end cap and is positioned at an equal distance from the holes through which the air is expelled.

9. The method of claim 8, wherein the needle is a hypotube.

10. The method of claim 8, wherein the chamber includes a spout positioned inside the chamber for receiving a segment of the needle when the end cap is connected to the chamber.

11. A method of coating a stent, comprising:

(a) providing a nozzle assembly capable of dispensing a stent coating composition, comprising:

an air chamber capable of receiving air from an atomizer for atomizing the composition as the composition is dispensed;

a nozzle, coupled to the air chamber, having a plurality of air outlets capable of expelling the air received from the atomizer via the air chamber to atomize the composition; and a hypotube disposed partially within a tube that carries the composition and extends through the air chamber, the hypotube capable of dispensing the composition onto a stent; and (b) applying a coating composition to the stent with the nozzle assembly.

12. The method of claim 11, wherein a segment of the hypotube extends out of the nozzle.

13. The method of claim 11, wherein the nozzle assembly enables external atomization of the coating composition.

14. The method of claim 11, wherein the plurality of air outlets include air outlets that circumscribe the hypotube.

15. The method of claim 11, wherein the tube is capable of being connected to a reservoir or a pump for dispensing the coating composition.

* * * * *